US005530037A

United States Patent [19]
McDonnell et al.

[11] Patent Number: 5,530,037
[45] Date of Patent: Jun. 25, 1996

[54] STERILIZED CYANOACRYLATE ADHESIVE COMPOSITION, AND A METHOD OF MAKING SUCH A COMPOSITION

[75] Inventors: Patrick F. McDonnell, Dublin; Robert J. Lambert, County Dublin, both of Ireland

[73] Assignee: Loctite (Ireland) Limited, Tallaght, Ireland

[21] Appl. No.: 360,511

[22] Filed: Dec. 21, 1994

[30] Foreign Application Priority Data

Dec. 23, 1993 [IE] Ireland .................................. 931009

[51] Int. Cl.⁶ ............................ C08J 3/28; C09J 4/04; C08K 5/13
[52] U.S. Cl. .................. 522/79; 522/74; 522/76; 522/173; 523/111; 514/527
[58] Field of Search .......................... 522/75, 79, 74, 522/152, 76, 81, 173; 252/404; 523/111; 574/527

[56] References Cited

U.S. PATENT DOCUMENTS

| 3,527,224 | 9/1970 | Rabinowitz | 128/334 |
|---|---|---|---|
| 3,699,127 | 10/1972 | O'Sullivan et al. | 260/33.2 |
| 4,100,141 | 7/1978 | O'Sullivan | 522/79 |
| 4,820,755 | 4/1989 | Webster | 522/79 |
| 5,403,591 | 4/1995 | Tighe et al. | 424/445 |

FOREIGN PATENT DOCUMENTS

| 1281457 | 7/1972 | United Kingdom | C07C 67/06 |
|---|---|---|---|
| WO81/00701 | 3/1981 | WIPO | B65D 39/00 |

OTHER PUBLICATIONS

Yves Hernon, "Gamma Processing: The State of the Art," *Medical Device Technology*, Jun./Jul. 1992, Publication No. 0010, pp. 30–37.

K. L. Shantha et al., "Developments and applications of cyanoacrylate adhesives," *J. Adhesion Sci. Technol.*, vol. 3, No. 4, pp. 237–260 (1989).

E. M. Al–Khawam et al., *Adhesion 7*, Applied Science Publishers, 1983, Chapter 6, "Cyanoacrylate Adhesives of Potential Medical Use," pp. 109–133, odd numbered pages only.

Chemical Abstract CA84(13):88097e, Mutsuo Ishizaki et al., "Degradation of food additives by irradiation," Khokuhin Eisenigaku Zasshi, 16(4), 1975, pp. 230–233.

Chemical Abstract CA98(14):108587j, East Ger. Patent No. DD 156365 18 Aug. 1982–Population Research, Inc., "Adhesive from 2–cyanacrylic acid methyl ester".

Chemical Abstract CA79(7):34851lm, K. F. Lindenau et al., "Animal experimental review of new tissue adhesives of fimomed potassium chloride," Deut. Gesundheitsw., 28(5), 1973, pp. 218–220.

Chemical Abstract CA79(2):9856x, Kalman Somogyvari, "Alloplastics," Acta Vet., 22(3), 1972, pp. 307–314.

*Primary Examiner*—Susan W. Berman
*Attorney, Agent, or Firm*—Vidas, Arrett & Steinkraus

[57] ABSTRACT

A curable cyanoacrylate adhesive composition intended for medical and/or veterinary uses is sterilized in liquid form by gamma irradiation. The composition comprises a) a cyanoacrylate monomer b) a combination of an anionic stabilizer and a free-radical stabilizer in amounts effective to stabilize the composition during irradiation and to stabilize the sterilized composition during storage prior to cure, wherein the free radical stabilizer is a selected phenolic antioxidant (but not including hydroquinone).

The preferred free radical stabilizer is butylated hydroxyanisole. After irradiation the cyanoacrylate monomer is substantially ungelled.

18 Claims, No Drawings

STERILIZED CYANOACRYLATE ADHESIVE COMPOSITION, AND A METHOD OF MAKING SUCH A COMPOSITION

BACKGROUND OF THE INVENTION

1) Field of the Invention

This invention relates to a sterilized cyanoacrylate adhesive composition, and to a method of making such a composition. The composition is suitable for bonding a wide range of substrates but is especially intended for medical and/or veterinary uses such as wound closure and general surgical applications.

2) Description of the Related Art

There is considerable experience in the use of cyanoacrylate adhesives in medical and veterinary practice (Shantha et al. "Developments and Applications of Cyanoacrylate Adhesives", J. Adhesion Sci. Technol Vol. 3, No. 4, pp 237–260 (1989)). Cyanoacrylate adhesives have been proposed for surgical treatment such as wound adhesives, hemostatics and tissue adhesives, particularly for sutureless skin bonding. It is desirable that an adhesive for medical or veterinary use should be sterilizable (Al-Khawan et al. "Cyanoacrylate adhesives of potential medical use", Adhesion 7 (Allen K. W.) Applied Science Publishers, Chap. 6, 109–133 (1983).

Cyanoacrylate adhesives must be stabilized against anionic and free radical polymerization. WO 8100701 Krall describes a methyl cyanoacrylate adhesive composition for sealing fallopian tubes in female sterilization containing a polymerisation inhibitor such as an organic carboxylic acid, $SO_2$ and an antioxidant selected from hydroquinone, hydroquinone mono-methyl ether, butylated hydroxyanisole and their mixtures.

A cyanoacrylate adhesive composition for medical use is commercially available under the Trade Mark HISTOACRYL BLUE from B. Braun Melsungen AG. This composition is not sterilized.

Several methods which are available for positively sterilising liquids could be considered for application to cyanoacrylate adhesives. These include ionising radiation (electron accelerators or gamma radiation from a radioactive source such as Cobalt 60 or Caesium 137), dry-heat, steam, gas, filtration and liquid sterilisation. Aseptic filling of the adhesive immediately following manufacture is also an option. Factors to consider in choosing a sterilisation method include (a) the reactive nature of cyanoacrylates, (b) contamination due to induced chemical changes in the adhesive composition, (c) subsequent storage stability, (d) effect on bonding performance (immediate and long-term), (e) viscosity changes, (f) effect on the package or vessel used to contain the adhesive and (g) the maintenance of sterility on storage up to the time of utilisation.

Most of the above sterilisation methods are unsuitable or suffer from severe limitations in their applicability to cyanoacrylate adhesives. Electron beam accelerators have relatively low penetrating ability and would be effective only in sterilising the outer surfaces of thee container or package. Dry-heat sterilisation generally involves a heating cycle at 160°–170° C. for 22 hours. This treatment would be extremely detrimental to cyanoacrylate adhesives with the strong likelihood that polymerisation would occur before the cycle was complete. Even if the adhesive survived (e.g. by incorporation of excessive levels of stabilizers) the treated product would have an adverse effect on performance and induce gross discoloration. Steam sterilisation using moist heat also involves exposure to an undesirably high temperature cycle (121°–141° C.) with the same adverse effects on the adhesive as mentioned above under the dry-heat process. In addition, the extreme sensitivity of cyanoacrylate adhesives to moisture would limit the adhesive container to a totally moisture impermeable package such as a sealed glass ampoule. Gas sterilisation usually involves the use of ethylene oxide. While this process can be carried out at relatively low temperatures the reactivity of the gas combined with that of the cyanoacrylate adhesives would induce rapid polymerisation and make the treatment unworkable. Sterilisation by filtration is not a viable method for cyanoacrylate adhesives because the pores of the filter will inevitably become blocked due to localised polymerisation. Likewise sterilisation by contact with a liquid such as formalin will only be effective on the outer surface of the container.

Aseptic filling of the adhesive direct from the final receiving vessel used in the distillation stage of manufacture would in theory yield a sterile product. This follows because the cyanoacrylate prepolymer is cracked at temperatures of over 190° C. in a sealed vessel during manufacture. The composition of the final adhesive would be very limited however, as necessary additives such as stabilizers could not be conveniently added and mixed in a controlled fashion. If required, viscosity modifiers such as polymethylmethacrylate would require heating in a separate vessel to achieve dissolution and this step would destroy the sterility.

Following on the unsuitable nature of the sterilisation methods discussed above it was decided to investigate the viability of using gamma irradiation from a Cobalt 60 source as an effective method of sterilising cyanoacrylate adhesives.

The gamma radiation emitted from a cobalt 60 source consists of high energy photons which have the ability to penetrate many materials including various plastics, liquids and metal foils. Any living microorganisms contaminating the product are deactivated and their metabolism and reproductive capabilities destroyed when they are exposed to a gamma radiation dose of 25 kGy. (Henon Y., "Gamma Processing, The State of the Art" in Medical Device Technology, June/July 1992, pages 30–37).

GB 1 281 457 (DE-OLS-2 055 658) Stehlik dating from November 1970 describes a process for irradiating monomeric or oligomeric esters of –cyanoacrylic acid for the purpose of sterlization of tissue binding adhesives. The monomers or oligomers may be stablized with from 0.001 to 0.14 by weight of a gaseous Lewis acid inhibitor, acids such as sulphur dioxide, nitrogen oxide, boron trifluoride and hydrogen fluoride, and with from 0.1 to 0.54 by weight of a phenolic free radical polymerisation inhibitor, preferably with a mixture of sulphur dioxide and hydroquinone. The patent states that as the monomeric or oligomeric compounds polymerise very readily, normal sterilisation processes including ionising radiation at room temperature are completely useless. The patent also teaches that sterilization by ionising radiation of the adhesive composition in liquid form deleteriously affects the properties of the adhesive to the extent that it becomes unuseable. The patent states that only when solid adhesive material is irradiated is it possible to prevent damage to the substance both as regards its surgical usefulness and its adhesive properties as well as viscosity and stability; the patentees therefore prefer to cool the monomeric or oligomeric compounds to a temperature of not more than –30° C. The three working examples in the patent are carried out at –196° C., –80° C. and –183° C. respectively. No stabilizers are used in any of the working examples. Example 1 states that an adhesive substance which was exposed to 0.2 Mrad (2 kGy) gamma-ray dose at room temperature polymerised completely.

To carry out irradiation at low enough temperatures to achieve solidification of the adhesive composition is not a practical proposition for industrial production. Sterilization should be performed on the liquid adhesive temperature at or near to room temperature.

A minimum dose requirement of 25 kGy (2.5 Mrad) gamma radiation is generally accepted as adequate for the purpose of sterilization (U.K. Department of Health "Quality Systems for Sterile Medical Devices and Surgical Products", 1990 Good Manufacturing Practice, HMSO, London). A dose of 2 kGy (0.2 Mrad) would be wholly inadequate for achieving sterilization.

U.S. Pat. No. 3,527,224 Rabinowitz describes a method of surgically bonding tissue using an adhesive composition based on n-pentyl alpha-cyanoacrylate which is subjected to partial polymerisation to increase its viscosity. Radiation such as gamma rays can be used to get both the desired partial polymerisation and sterilization in a one-step process. However a free-radical inhibitor must be introduced into the composition after the irradiation, with the risk of introducing bacterial contamination. The method of thickening would be difficult to quench effectively after the desired viscosity is achieved.

The present Applicants have invented a sterilized adhesive composition which contains monomeric cyanoacrylate in a substantially ungelled condition and which therefore is of low viscosity. The composition contains all of the necessary ingredients before it is sterilized by irradiation. The composition can be readily and fully sterilized by gamma irradiation with a minimum dose of 25 kGy (2.5 Mrad) at room temperature without any significant increase in viscosity while mantaining the necessary performance and shelf-life of the adhesive.

Hydroquinone is generally used as the free-radical stabilizer for cyanoacrylate adhesives under normal ageing conditions. If a sufficient concentration (e.g. 500–1000 ppm) is present it will also be an effective stabilizer to prevent polymerisation during gamma irradiation treatments. However chemical changes to the hydroquinone molecule occur during the treatment, resulting in the conversion of approximately 25% of the hydroquinone to 1,4-benzoquinone. This material is known to be toxic and its presence in an adhesive, especially if used for medical applications, would be undesirable.

It is an object of the present invention to provide a sterilized cyanoacrylate composition which does not have the disadvantages discussed above.

It is a particular object of the invention to provide a sterilized cyanoacrylate composition which is substantially free of toxic contaminants, especially 1,4-benzoquinone.

SUMMARY OF THE INVENTION

The present invention provides a curable cyanoacrylate adhesive composition for use in bonding, wherein the composition has been sterilized in liquid form by gamma irradiation and is the irradiation product of a composition comprising a) a cyanoacrylate monomer; and b) a combination of an anionic stabliser and a free-radical stabilizer in amounts effective to stabilize the composition during irradiation and to stabilize the sterilized composition during storage prior to cure, wherein the free-radical stabilizer is a phenolic antioxidant selected from compounds of the formula I and II:

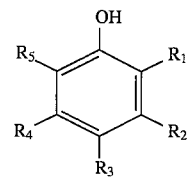

wherein $R_5$ is —H, an alkyl group having 1 to 20 carbon atoms, an alkenyl group having 2 to 20 carbon atoms or an aryl group having 6 to 36 carbon atoms;

$R_1$, $R_2$, $R_3$ and $R_4$, which may be the same or different, are each $R_5$ or —$OR_5$;

provided that when $R_1$, $R_2$, $R_4$ and $R_5$ are each —H, $R_3$ is not —OH;

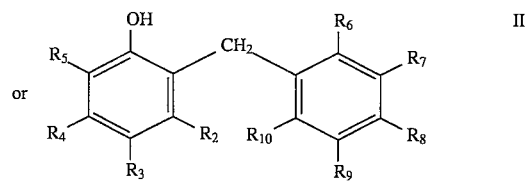

wherein $R_2$, $R_3$, $R_4$ and $R_5$ are as hereinbefore defined;

$R_6$, $R_7$, $R_8$, $R_9$ and $R_{10}$, which may be the same or different are each $R_5$ or —$OR_5$;

the cyanoacrylate monomer in the stabilized liquid composition after irradiation being substantially ungelled.

The invention further provides a method of making a curable sterile cyanoacrylate adhesive composition for use in bonding which comprises preparing a liquid composition comprising (a) a cyanoacrylate monomer (b) a combination of an anionic stabilizer and a free-radical stabilizer in amounts effective to stabilize the composition during sterilization by gamma irradiation and to stabilize the sterilized composition during storage prior to cure, wherein the free-radical stabilizer is a phenolic antioxidant selected from compounds of the formula I or II as defined above, and exposing the composition in liquid form to gamma irradiation in a dose sufficient to sterilize the composition without substantial gelling of the cyanoacrylate monomer.

In the compounds of Formula I or II an alkyl or alkenyl group preferably has up to 10 carbon atoms, more particularly up to 5 carbon atoms, most preferably up to 4 carbon atoms, and an aryl group preferably has up to 20 carbon atoms, more particularly up to 10 carbon atoms.

In particularly preferred compounds of Formula I or II, at least one of $R_1$, $R_2$, $R_4$ and $R_5$ (and in the case of compounds of Formula II at least one of $R_7$, $R_8$ and $R_{10}$) is —$C(CH_3)_3$. Preferably also, $R_3$ (and in the case of compounds of Formula II also $R_9$) is selected from —$CH_3$ and —$OCH_3$.

The most preferred compound of Formula I is butylated hydroxyanisole (BHA) which is a blend of isomers (2-tert-butyl-4-methoxy phenol and 3-tert-butyl-4-methoxy phenol).

The preferred cyanoacrylate monomers are alkyl, alkenyl and alkoxy cyanoacrylate esters, more particularly such esters wherein the alkyl or alkenyl group has up to 10 carbon atoms, especially up to 5 carbon atoms.

The cyanoacrylate monomer may be selected from methyl, ethyl, n-propyl, iso-propyl, n-butyl, iso-butyl, sec-butyl, tert-butyl, n-pentyl, iso-pentyl, n-hexyl, iso-hexyl, n-heptyl, iso-heptyl, n-octyl, n-nonyl, allyl, methoxyethyl, ethoxyethyl, 3-methoxybutyl and methoxyisopropyl cyanoacrylate esters.

The preferred monomers are n-butyl, iso-butyl and sec-butyl cyanoacrylates because of their well known ability to bond tissue, bone tendons, etc. Other cyanoacrylate esters such as methyl, ethyl, n-propyl, n-hexyl, n-heptyl, n-octyl can also be used in such applications but suffer from certain disadvantages; e.g. methyl, ethyl and n-propyl cyanoacrylates have less satisfactory spreadibility on wound areas and tend to induce localised inflammation. The higher homologues are well tolerated by the tissues but they are slower curing, give weaker bond strengths and are generally more difficult to synthesise on a commercial basis. n-Butyl cyanoacrylate is preferred for the compositions of this invention.

The preferred method of the invention involves firstly the manufacture of an alkyl cyanoacrylate adhesive monomer, e.g. n-butyl cyanoacrylate, to a high and reproducible state of purity using the Knoevenagel reaction between the corresponding alkyl cyanoacetate and paraformaldehyde followed by pyrolysis and distillation to remove process contaminants. Anionic stabilizers, free-radical stabilizers, and optionally thickeners, dyes, thixotropic agents, etc. are added as required. The adhesive formulations are then packed into suitable bottles, tubes, vials etc. The filled bottles are then sealed in metal foil (e.g. aluminium foil) pouches and subjected to gamma irradiation with a dose of 25 kGy under conventional conditions i.e. at room temperature. Following this treatment the adhesives and untreated controls are fully assayed and evaluated for bonding performance, viscosity, shelf life and especially any chemical changes which may have occurred during the irradiation stage.

A range of alternative anti-oxidants were evaluated for their ability to stabilize n-butyl cyanoacrylate under normal conditions (see Example No. 3) and after gamma irradiation treatment (see Example No. 4). From examination of these findings on the basis of solubility, accelerated stability, condition after irradiation and toxicity considerations, it was found that butylated hydroxyanisole (BHA) was most suitable. During the irradiation treatment approximately 900 ppm of BHA is degraded with the formation of a number of derivatives. These have been identified and none are deemed to be harmful (Ishizaki et al., Shokuhin Eiseigaku Zasshi, 16(4), 230–3). BHA is a well known pharmacopoieal substance which is widely used as an anti-oxidant in foods and medicines and poses no significant toxicological hazard. The useful concentrations of BHA needed for the compositions of this invention are usually in the range 1000–5000 ppm. Variations may occur in the stability of the raw cyanoacrylate monomer from batch to batch, and levels of the antioxidant may be adjusted accordingly. Preferred concentrations are in the range 1500–3500 ppm, particularly above 2000 ppm. At levels less than 1000 ppm the adhesive may solidify or thicken excessively during radiation treatment due to the degradiation of 900 ppm as discussed above. At levels greater than 5000 ppm there is no additional benefit in the stabilizing effect.

Another preferred antioxidant is butyl hydroxy toluene (BHT, or 4-methyl-2,6-di-tert-butylphenol) which is also a well known antioxidant for food and therefore is non-toxic. However it needs to be used in larger amounts than BHA e.g. more than 2000 ppm and particularly above 2500 ppm.

Other anti-oxidants which may be used include methyl hydroquinone, catechol, tert-butyl hydroquinone, 4-tert-butoxyphenol, 4-ethoxyphenol, 3-methoxyphenol, 2-tert-butyl-4-methoxyphenol, and 2,2-methylene-bis-(4-methyl-6-tert-butylphenol). These antioxidants may be used in different concentrations from BHA but generally in the range 500 to 10,000 ppm. The appropriate concentration can be determined by testing along the lines described below.

Known anionic (acid) stabilizers for cyanoacrylate adhesives include Sulphur Dioxide, Sulphonic Acids, Sulphuric Acid, Sulphur Trioxide, Phosphorous Acids, Carboxylic Acids, Picric Acid, Boron Trifluoride, $BF_3$-ether complexes, Citric Acid, Hydrofluoric Acid, Tin (IV) Chloride, Iron (III) Chloride, and mixtures of two or more thereof.

Sulphur dioxide is particularly well known as a satisfactory stabilizer for cyanoacrylate adhesives under normal conditions of storage and use. Sulphur dioxide was also found to be a satisfactory anionic stabilizer during gamma irradiation treatment (EXAMPLE 6). The fate of sulphur dioxide during gamma irradiation was also investigated. It was found that all the sulphur dioxide remaining in the adhesive after irradiation was in the form of sulphuric acid. A proportion of the stabilizer was also found to be consumed during the treatment as it acted in its normal role as a polymerisation inhibitor (see Example No 6). The initial concentrations of sulphur dioxide needed to stabilize the adhesive compositions of this invention are in the range 20–150 ppm. Preferred concentrations are in the range 40–120 ppm. At levels less than 20 ppm the adhesives may solidify or thicken excessively during irradiation or there may be insufficient sulphur dioxide remaining to give a useful shelf-life after irradiation. The composition after irradiation should preferably contain sulphuric acid in an amount equivalent to at least 16 ppm of $SO_2$. At levels higher than 150 ppm the cure speed and general performance of the adhesive may be adversely impaired (see Example No 6). Concentration levels for other anionic stabilizers which are strong acids such as sulphonic acids, sulphuric acid, $BF_3$ etc. are likely to be in the range of 15 to 150 ppm, and for weaker acids such as carboxylic acids are likely to be in the range of 25 to 500 ppm.

As already noted, the stability of the raw cyanoacrylate monomer may vary from batch to batch, and levels of antioxidant and/or anionic stabilizer may be adjusted accordingly.

The bond strength and cure speed of the adhesive compositions described in this application were determined on nylon 66 (a polyamide with a chemical reaction simulating skin in the context of bonding with cyanoacrylate adhesives) and pig skin. In each case adequate strengths and cure speeds were obtained. (see Example No. 6 and Example No. 7).

While cyanoacrylate adhesives can be manufactured to a very high state of purity this standard may be compromised to meet the minimum requirements of industrial or consumer instant adhesives. No such compromise would be acceptable for adhesives supplied for medical and veterinary applications. It is therefore desirable that the concentrations of all impurities should be identified where practical and minimised by careful control of the manufacturing process. The adhesive compositions of this invention were assayed for total purity before and after sterilisation by gamma irradiation at a dose of 25–35 kGy. (Example No 7). The effect of room temperature and refrigerated ageing on the levels of these impurities are also included in Example No. 7.

Conventional additives such as thickeners, dyes and thixotropic agents may be included in the compositions as required. However for medical or veterinary use care must be taken to ensure that additives do not introduce toxic contaminants which survive or are produced by irradiation.

Polymethyl methacrylate, for example, may contain a residue of peroxide. Irradiation may itself cause some thickening of the composition. For medical or veterinary use a maximum composition viscosity after irradiation of about 200 mPas is desirable, preferably less than 50 mPas, especially less than 25 mPas.

The adhesive compositions of this invention will retain their usability in bonding applications for extended periods at room temperature but are preferably stored under refrigeration for maximum shelf-life (see Example No 7). When packaged in screw-cap bottles or tubes, an outer sealed metal foil pouch is required to preserve sterility. This barrier also prevents absorption of atmospheric moisture which can initiate premature gellation of the adhesive.

The invention discloses a process and a formulation resulting in a shelf-stable, sterilisable cyanoacrylate adhesive which can be used for the bonding of tissue in medical and veterinary applications.

The term "ppm" as used in this specification means parts per million by weight.

All irradiation treatments in the following Examples were carried out in conventional manner at ambient temperature.

DESCRIPTION OF THE PREFERRED EMBODIMENTS

EXAMPLE 1

(Comparative)

A batch of n-Butylcyanoacrylate (BCA) was distilled under reduced pressure of 1 mg Hg. The distillate was collected in a receiving vessel containing a concentrated solution of sulphur dioxide ($SO_2$) in a small volume of previously purified BCA monomer. The yield of distillate was weighed and the concentration of $SO_2$ adjusted to 0.0100% (100 ppm).

This stabilized control BCA monomer was then divided into a number of parts. To these parts was added hydroquinone (free radical stabilizer) to give the following series of samples containing the stated concentrations of hydroquinone (HQ).

| Sample A | 0.05% | (500 ppm) HQ |
| Sample B | 0.1406% | (1406 ppm) HO |
| Sample C | 0.1580% | (1580 ppm) HQ |
| Sample D | 0.1714% | (1714 ppm) HQ |
| Sample E | 0.2560% | (2560 ppm) HQ |
| Sample F | 0.2574% | (2574 ppm) HQ |

Portions of sample A to F were packed into small plastic bottles with screw cap closure. Each bottle was enclosed in an aluminium foil sachet which was heat sealed. The sachets and contents were then subjected to a gamma irradiation treatment, using a cobalt 60 source, with a dose of 25 Kilogray (kGy).

After treatment the samples were removed from the sachets and examined visually. Sample A was found to have solidified. Samples B to F inclusive were low viscosity on inspection and the HQ content was assayed by the HPLC technique. The HQ concentrations before and after irradiation were as follows:

TABLE 1

| Sample Ref. | HQ (ppm) | |
|---|---|---|
| | Before Irradiation | After Irradiation |
| A | 500 | Solidified |
| B | 1406 | 812 |
| C | 1580 | 988 |
| D | 1714 | 953 |
| E | 2560 | 1782 |
| F | 2574 | 1857 |

The results show a reduction in HQ concentration following gamma irradiation.

EXAMPLE 2

(Comparative)

A sample of BCA containing 53 ppm $SO_2$ and 2983 ppm HQ was prepared as described in Example 1. A portion of the sample was subjected to a gamma irradiation dose of 25 kGy under the conditions described in Example 1.

Both the untreated control and the irradiated sample were assayed to determine if any chemical or physical changes had occurred during the treatment. Results of the assay are in TABLE 2.

TABLE 2

| | Untreated Control | Irradiated |
|---|---|---|
| HQ (ppm) | 2983 | 2076 |
| $SO_2$ (ppm) | 53 | ND |
| $H_2SO_4$ (ppm) | ND | 60 |
| 1,4-Benzoquinone | ND | 552 |
| n-Butylcyanoacetate (%) | 0.20 | 0.20 |
| Viscosity (mPaS) | 2.4 | 7.4 |

The detectable chemical and physical changes in the BCA composition following irradiation can be summarized as follows:

(a) Approximately 25% of the hydroquinone was converted to 1,4-benzoquinone.

(b) All the $SO_2$ was converted to sulphuric acid with 13 ppm of $SO_2$ being consumed.

(c) The viscosity of the BCA monomer increased from 2.4 to 7.4 mPaS.

EXAMPLE 3

(Stability Tests Without Irradiation)

A batch of BCA monomer was prepared as in Example 1 and stabilized with 100 ppm $SO_2$. No free radical stabilizer was added at this stage.

The batch of $SO_2$ stabilized BCA monomer was then sub-divided into a number of parts to each of which was added a known antioxidant material at a concentration of 0.54. These were mixed at room temperature and all dissolved readily in BCA monomer except 4-tert-butoxyphenol. This material had poor solubility even after mixing and heating for an extended period.

The efficiency of the antioxidants to act as free radical stabilizer in BCA was assessed by aging small samples of each antioxidant solution in corked glass tubes at 80° C. and 55° C. (in air circulating ovens). The time for gellation or solidification to occur was determined by daily inspection. The Gel Time results are summarized in TABLE 3.

TABLE 3

| Antioxidant | Gel Time (Days) | |
|---|---|---|
| (0.5% in BCA) | 80° C. | 55° C. |
| Butyrated Hydroxy Anisole | 18–19 | 83–89 |
| Butylated Hydroxy Toluene | 15–18 | 83–89 |
| Methyl Hydroquinone | 19–20 | 90–97 |
| Catechol | 20–22 | 104–108 |
| tert-Butylhydroquinone | 4–7 | 89–90 |
| 4-tert-Butoxyphenol | 1–3 | 10–12 |
| 4-Ethoxyphenol | 19–20 | 90–92 |
| 3-Methoxyphenol | 10–11 | 83–89 |
| 2-tert-Butyl-4-methoxyphenol | 18–19 | 83–89 |
| Hydroquinone | 24–25 | 104–108 |

The above results, under accelerated conditions, predict with a few exceptions, that most of the antioxidants evaluated would be effective free-radical stabilizers for BCA. The results also confirm that Hydroquinone is most effective in this regard. It is widely used to stabilize cyanoacrylate adhesives for industrial and household use. However it is unsuitable for use in a composition for irradiation for the reasons shown in Example 2.

EXAMPLE 4

A batch of BCA monomer was prepared, free of antioxidants, by vacuum distillation at 1 mg Hg. Distillation of 631.1 g of relatively impure BCA gave 436 g of purified material. This was collected in a receiver containing sufficient $SO_2$ concentrate to give a final concentration of 100 ppm $SO_2$.

Solutions of various antioxidants were prepared in above BCA monomer at concentrations between 1000 ppm and 10,000 ppm. Details of the test solutions are in TABLE 4.

Samples of each test solution were packed in small polyethylene bottles with screw-cap closures which were overwrapped individually in sealed aluminium foil pouches. The packaged samples were treated by gamma irradiation at a dose of 28.53 kGy. The viscosity of each test solution was determined before and after irradiation. The results are summarized below in TABLE 4.

TABLE 4

| TEST SOLUTION DETAILS | | VISCOSITY mPas | |
|---|---|---|---|
| | | Before | After |
| Ref. No. | ANTIOXIDANT | Conc. ppm | Irradi- ation | Irradi- ation |
| 1 | 2,2'-methylenebis(4-methyl-6-tert-butylphenol) | 2490 | 3.4 | Gelled |
| 2 | 2,2'-methylenebis(4-methyl-6-tert-butylphenol) | 4970 | 3.4 | Soft Gel |
| 3 | 2,2'-methylenebis(4-methyl-6-tert-butylphenol) | 10000 | 3.4 | 267.0 |
| 4 | Catechol | 5000 | 3.4 | 9.9 |
| 5 | t-Butylhydroquinone | 5000 | 3.4 | 3.4 |
| 6 | 4-Ethoxyphenol | 5000 | 3.4 | 14.1 |
| 7 | 3-Methoxyphenol | 5000 | 3.4 | Gelled |
| 8 | Butylated hydroxyanisole | 1000 | 3.4 | Gelled |
| 9 | Butylated hydroxyanisole | 2500 | 3.4 | 4.9 |
| 10 | Butylated hydroxytoluene | 1500 | 3.4 | Gelled |
| 11 | Methyl hydroquinone | 1500 | 3.4 | Soft gel |

TABLE 4-continued

| TEST SOLUTION DETAILS | | VISCOSITY mPas | |
|---|---|---|---|
| | | Before | After |
| Ref. No. | ANTIOXIDANT | Conc. ppm | Irradi- ation | Irradi- ation |
| 12 | Hydroquinone | 1500 | 3.4 | 17.8 |

The above trials demonstrate that selection of both the type and concentration of antioxidant is necessary to obtain an efficient free radical stabilizer for BCA to prevent gellation during gamma irradiation treatment. Butylated hydroxyanisole (BHA) at a concentration substantially above 1000 ppm before irradiation is the most suitable, with the preferred level being 2500 ppm. For butylated hydroxytoluene (BHT) a higher concentration is needed than for BHA. Hydroquinone is effective as a stabilizer at relatively low levels. Derivatives of hydroquinone which do not have toxic break-down products may be selected by tests as described above.

EXAMPLE 5

A batch of Ethyl Cyanoacrylate monomer was prepared using the techniques described in Example 1 and used as the basis of formulations A and B which had the following compositions:

A. Ethyl cyanoacrylate stabilized with 20 ppm Boron Trifluoride and 5000 ppm Hydroquinone and thickened to a viscosity of 30 mPas by addition of 5% by weight of finely powdered polymethylmethacrylate.

B. The same as formulation A above but with 20 ppm $SO_2$ added.

Samples from each formulation were packaged in small polyethylene bottles with screw-cap closures and subjected to a sterilization process consisting of gamma irradiation from a Cobalt 60 source at a dose of 25 kilogray (kGy). After sterilization treatment the samples were examined visually and no significant change in viscosity was observed in either case. This example illustrates the successful sterilization of a cyanoacrylate adhesive containing thickener and anionic stabilizers alone or in combination and in conjunction with an effective concentration of a free radical stabilizer.

EXAMPLE 6

A batch of BCA monomer was distilled as in Example i and stabilized with various levels of $SO_2$ and BHA as detailed below in Table 5.

TABLE 5

| BCA Composition Ref. | BHA (ppm) | $SO_2$ (ppm) |
|---|---|---|
| 1 | 3034 | 31 |
| 2 | 2997 | 42 |
| 3 | 3189 | 50.4 |
| 4 | 3289 | 66.7 |
| 5 | 3267 | 79.8 |
| 6 | 3229 | 94 |

Samples of each liquid composition were packed in polyethylene bottles, overwrapped with sealed aluminium foil pouches and treated with gamma irradiation at a dosage of 25 kGy.

The irradiated samples and untreated controls were tested as follows:

(a) BHA assay by HPLC.
(b) $SO_2$ or $H_2SO_4$ by potentiometric Titration.
(c) Viscosity by Cannon Fenske capillary viscometer method.
(d) Bond strength on Nylon 66 lapshears of dimensions 100 mm × 25 mm × 2 mm with an overlap bonded area of 312.5 mm$^2$. The bonds were clamped and cured for 24 hours at RT. The bond strength was determined using a Tensile testing machine at a crosshead speed of 2 mm/min.
(e) Time to gel when aged in glass test tubes at 82° C. in an air circulating oven.
(f) Time to gel when aged in a polyethylene bottle at 55° C. in an air circulating oven.

See Test results before irradiation (Table 6A) and after irradiation (Table 6B).

TABLE 6A (Before Irradiation)

| BCA Composition Ref. No. | BHA (ppm) | $SO_2$ (ppm) | Viscosity (mPaS) | Bond Strength Nylon 66 (daNcm$^{-2}$) | Gel Time at 82° C. (days) | Gel Time at 55° C. (days) |
|---|---|---|---|---|---|---|
| 1 | 3034 | 31 | 13.7 | 25 | 10+ | 50+ |
| 2 | 2997 | 42 | 14.2 | 27 | 10+ | 50+ |
| 3 | 3189 | 50.4 | 14.5 | 32 | 10+ | 50+ |
| 4 | 3289 | 66.7 | 14.5 | 26 | 10+ | 50+ |
| 5 | 3267 | 79.8 | 14.5 | 24 | 10+ | 50+ |
| 6 | 3229 | 94 | 14.5 | 24 | 10+ | 50+ |

TABLE 6B (After Irradiation)

| BCA Composition Ref. No. | BHA (ppm) | $SO_2$ (ppm) | Viscosity (mPaS) | Bond Strength Nylon 66 (daNcm$^{-2}$) | Gel Time at 82° C. (days) | Gel Time at 55° C. (days) |
|---|---|---|---|---|---|---|
| 1 | 1995 | 2 | 9.4 | 21 | 1.5 | <14 |
| 2 | 1992 | 7 | 9.7 | 23 | 2.5 | <14 |
| 3 | 2131 | 16 | 10.0 | 23 | 5.5 | 27 |
| 4 | 1917 | 20 | 10.6 | 22 | 8.5 | 41 |
| 5 | 2142 | 32 | 10.6 | 19 | 8.5 | 49.5 |
| 6 | 2046 | 42 | 10.8 | 17 | 8.5 | 49.5 |

The result of above trials show that BCA monomer stabilized with about 3000 ppm BHA and > 50 ppm $SO_2$ gives a composition which is stable after gamma irradiation of dose 25 kGy (Data at 55° C. + 82° C.).

EXAMPLE 7

A formulation of n-butyl cyanoacrylate monomer was prepared as described earlier and 2500 ppm BHA and 102 ppm $SO_2$ added as stabilizers.

A sample of the batch was packed into polyethylene bottles, overwrapped with hermetically sealed aluminium foil sachets.

The sachets and liquid contents were then sterilised by gamma irradiation at a dose of 29 kGy.

A sample was tested (as detailed below) immediately after the irradiation treatment. A further sample was aged for 2 years at 4° C. and the tests repeated (Table 7).

The tests included assays for BHA, $SO_2$, viscosity and bond strength on Nylon 66 and the test methods are described in Example No. 7. Total purity as BCA was determined by gas chromotography.

Fixture time on pig skin was the time needed to give a bond with handling strength on this biological substrate.

TABLE 7

| | TESTED AFTER IRRADIATION | |
|---|---|---|
| ASSAY | Initial | 2 Years at 4° C. |
| Purity (% BCA) | 98.80 | 98.79 |
| BHA (ppm) | 1014 | 240 |
| $SO_2$ (ppm) | 126* | 114* |
| Bond Strength on Nylon (daNcm$^{-2}$) | 12.0 | 9.0 |
| Fixture time on Pig Skin (secs) | 12 | 15 |
| Viscosity (mPaS) | 4.7 | 5.9 |

*Titrated as $H_2SO_4$

The results show excellent retention of bonding performance on extended aging with no significant change in overall purity.

EXAMPLE 8

A batch of an adhesive formulation consisting of n-butyl cyanoacrylate monomer was prepared as described earlier and 2500 ppm BHA and 80 ppm $SO_2$ added as stabilizers.

The batch was packed down and overwrapped as described in Example 7.

The packed down product was then sterilized by gamma radiation from Cobalt 60 radioisotopic source with a dose of 25 kGy minimum and 35 kGy maximum.

The sterile liquid adhesive was then used to close wounds on 64 patients who had undergone a variety of operations involving surgical incisions, mainly to abdominal areas. The adhesive was applied using either the nozzle on the plastic bottle or alternatively a controlled pump dispenser e.g. a peristaltic pump. All materials in contact with the adhesive were previously sterilized to ensure that the adhesive remained sterile as it was applied to the wound area.

This method of wound closure gave transparent or translucent bonds without the need for additional dressings or bandages and with the added benefit of easy post-operative inspection by medical staff.

In all above cases the adhesive was found to be a safe and reliable method of wound closure.

We claim:

1. A curable cyanoacrylate adhesive composition for use in bonding, wherein the composition has been sterilized in liquid form by gamma irradiation of at least 25 kGy and is the irradiation product of a composition comprising
   a) a cyanoacrylate monomer; and
   b) a combination of an anionic stabilizer and a free-radical stabilizer in amounts effective to stabilize the composition during irradiation and to stabilize the sterilized composition during storage prior to cure,
wherein the free-radical stabilizer is a phenolic antioxidant selected from compounds of the formula I and II:

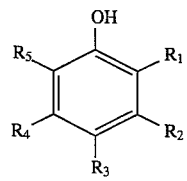

wherein
   $R_5$ is —H, an alkyl group having 1 to 20 carbon atoms, an alkenyl group having 2 to 20 carbon atoms or an aryl group having 6 to 36 carbon atoms; and
   $R_1$, $R_2$, $R_3$, and $R_4$, which may be the same or different, are each $R_5$ or —$OR_5$; provided that when $R_1$, $R_2$, $R_4$, and $R_5$ are each —H, $R_3$ is not —OH; or

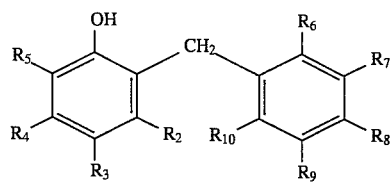

wherein
   $R_2$, $R_3$, $R_4$, and $R_5$ are as hereinbefore defined; and
   $R_6$, $R_7$, $R_8$, $R_9$, and $R_{10}$, which may be the same or different are each $R_5$ or —$OR_5$;
the cyanoacrylate monomer in the sterilized liquid composition after irradiation being substantially ungelled.

2. A composition according to claim 1 wherein, in the compounds of Formula I or II, at least one of $R_1$, $R_2$, $R_4$ and $R_5$ is —$C(CH_3)_3$ and in the case of compounds of Formula II at least one of $R_7$, $R_8$, and $R_{10}$ is also —$C(CH_3)_3$.

3. A composition according to claim 1 wherein, in the compounds of Formula I or II, R3 is selected from —$CH_3$ and —$OCH_3$, and in the compounds of Formula II $R_9$ is also selected from $CH_3$ and —$OCH_3$.

4. A composition according to claim 1 wherein the compound of Formula I is butylated hydroxyanisole.

5. A composition according to claim 4 wherein the butylated hydroxyanisole was present in an amount of above 1000 parts per million by weight before irradiation.

6. A composition according to claim 5 wherein the butylated hydroxyanisole was present in an amount of above 1500 parts per million by weight before irradiation.

7. A composition according to claim 1 wherein the cyanoacrylate monomer is selected from n-butyl, iso-butyl and sec-butyl cyanoacrylates.

8. A composition according to claim 1 wherein the cyanoacrylate monomer has been prepared by the Knoevenagel reaction between the corresponding alkyl cyanoacetate and paraformaldehyde followed by pyrolysis and distillation to remove process contaminants.

9. A composition according to claim 1 wherein the anionic stabilizer is sulphur dioxide or sulphuric acid.

10. A composition according to claim 9 wherein the sulphur dioxide was present in an amount in an amount in the range 20 to 150 parts per million by weight before irradiation.

11. A method of making a curable sterile cyanoacrylate adhesive composition for use in bonding which comprises preparing a liquid composition comprising
   (a) a cyanoacrylate monomer
   (b) a combination of an anionic stabilizer and a free-radical stabilizer in amounts effective to stabilize the composition during sterilization by gamma irradiation and to stabilize the sterilized composition during storage prior to cure,
wherein the free-radical stabilizer is a phenolic antioxidant selected from compounds of the formula I or II;

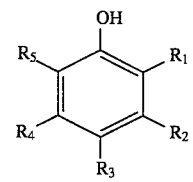

wherein
   $R_5$ is —H, an alkyl group having 1 to 20 carbon atoms, an alkenyl group having 2 to 20 carbon atoms or an aryl group having 6 to 36 carbon atoms and $R_1$, $R_2$, $R_3$, and $R_4$, which may be the same or different, are each $R_5$ or —$OR_5$, provided that when $R_1$, $R_2$, $R_4$, and $R_5$ are each —H, $R_3$ is not —OH; or

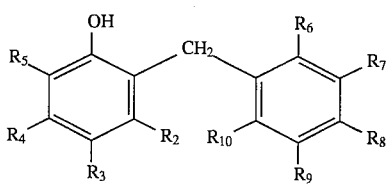

wherein $R_2$, $R_3$, $R_4$, and $R_5$ are as hereinbefore defined and $R_6$, $R_7$, $R_8$, $R_9$, and $R_{10}$, which may be the same or different, are each $R_5$ or —$OR_5$;

and exposing the composition in liquid form to gamma irradiation in a dose of at least 25 kGy without substantial gelling of the cyanoacrylate monomer.

12. A method according to claim 11 wherein the anionic stabiliser is present in the composition prior to irradiation in an amount in the range 15 to 500 parts per million by weight of the composition.

13. A method according to claim 12 wherein the anionic stabiliser is present in an amount in the range 40–120 parts per million.

14. A method according to claim 11 wherein the phenolic antioxidant is present in the composition prior to irradiation in an amount of at least 1500 parts per million by weight of the composition.

15. A method according to claim 14 wherein the phenolic antioxidant is butylated hydroxyanisole in an amount above 2000 parts per million.

16. A method as in claim 11, wherein the composition is exposed to a dose of gamma irradiation that is in the range of 25–35 kGy.

17. A composition according to claim 1 wherein the cyanoacrylate monomer is n-butyl cyanoacrylate.

18. A composition as in claim 1, wherein the free-radical stabilizer is 2,2'-methylenebis(4-methyl-6-tert-butylphenol) in an amount in excess of 4970 parts per million.

* * * * *

UNITED STATES PATENT AND TRADEMARK OFFICE
CERTIFICATE OF CORRECTION

PATENT NO. : 5,530,037

DATED : June 25, 1996

INVENTOR(S) : McDonnell et al

It is certified that error appears in the above-identified patent and that said Letters Patent is hereby corrected as shown below:

Col. 8, line 60, delete "0.54" and insert -- 0.5% --

Signed and Sealed this

Third Day of September, 1996

Attest:

BRUCE LEHMAN

Attesting Officer

Commissioner of Patents and Trademarks